(12) United States Patent
Baik et al.

(10) Patent No.: US 9,163,994 B2
(45) Date of Patent: Oct. 20, 2015

(54) ELECTRONIC MIRROR AND METHOD FOR DISPLAYING IMAGE USING THE SAME

(75) Inventors: Chan Wook Baik, Seongnam-si (KR); Sun il Kim, Seoul (KR); Changwon Lee, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 1122 days.

(21) Appl. No.: 12/385,908

(22) Filed: Apr. 23, 2009

(65) Prior Publication Data
US 2010/0188315 A1    Jul. 29, 2010

(30) Foreign Application Priority Data

Jan. 23, 2009    (KR) ........................ 10-2009-0006113

(51) Int. Cl.
*G09G 3/00*    (2006.01)
*G01J 5/02*    (2006.01)
*A61B 5/01*    (2006.01)
*G01J 5/08*    (2006.01)
*G01J 5/00*    (2006.01)

(52) U.S. Cl.
CPC ... *G01J 5/02* (2013.01); *A61B 5/01* (2013.01); *A61B 5/015* (2013.01); *G01J 5/025* (2013.01); *G01J 5/08* (2013.01); *G01J 5/0821* (2013.01); *G01J 5/0837* (2013.01); *G01J 5/0896* (2013.01); *G01J 5/0025* (2013.01); *G01J 2005/0077* (2013.01)

(58) Field of Classification Search
CPC ............. G09G 3/00; G09G 3/35; H01L 25/16
USPC .............. 345/32, 156, 104; 257/432; 398/115
See application file for complete search history.

(56) References Cited

U.S. PATENT DOCUMENTS

| 3,973,124 A | 8/1976 | Astheimer |
| 4,691,712 A | 9/1987 | Brown, Jr. |
| 7,697,053 B2 * | 4/2010 | Kurtz et al. ............... 348/333.01 |

(Continued)

FOREIGN PATENT DOCUMENTS

| DE | 20 2005 003 306 | 6/2005 |
| JP | 2000-83779 | 3/2000 |

(Continued)

OTHER PUBLICATIONS

Search Report for corresponding European Application No. 09161724.1 dated Nov. 10, 2009.

*Primary Examiner* — Quan-Zhen Wang
*Assistant Examiner* — Yuk Chow
(74) *Attorney, Agent, or Firm* — Harness, Dickey & Pierce, P.L.C.

(57) ABSTRACT

An electronic mirror and a method for displaying an image using the electronic mirror are provided. The electronic mirror may include a display unit, a detecting unit and a control unit. The detecting unit may receive a signal transmitted from the outside. The control unit may control the detecting unit and the display unit to display the signal received at the detecting unit on the display unit as an image. The image displayed on the display unit may be output from the electronic mirror through the detecting unit. The electronic mirror may further include a reflecting unit. A light from the outside may pass through the detecting unit and the display unit and then be reflected on the reflecting unit. The reflected light may be output from the electronic mirror through the display unit and the detecting unit.

26 Claims, 6 Drawing Sheets

(56) References Cited

U.S. PATENT DOCUMENTS

| | | |
|---|---|---|
| 7,714,923 B2 * | 5/2010 | Cok et al. ............... 348/333.01 |
| 2004/0008992 A1 * | 1/2004 | Nishimura ................. 398/115 |
| 2004/0075637 A1 * | 4/2004 | Izumi ........................ 345/104 |
| 2005/0018140 A1 | 1/2005 | Ishizaki et al. |
| 2005/0206610 A1 * | 9/2005 | Cordelli ..................... 345/156 |
| 2007/0040033 A1 * | 2/2007 | Rosenberg ............. 235/462.36 |
| 2008/0012084 A1 * | 1/2008 | Kwon et al. ............... 257/432 |

FOREIGN PATENT DOCUMENTS

| | | |
|---|---|---|
| JP | 2004-138768 A | 5/2004 |
| JP | 2005-65812 | 3/2005 |
| KR | 2004-0111137 A | 12/2004 |
| KR | 2005-0024303 A | 3/2005 |
| KR | 10-2007-0061783 | 6/2007 |
| KR | 10-2008-0080935 | 9/2008 |

* cited by examiner

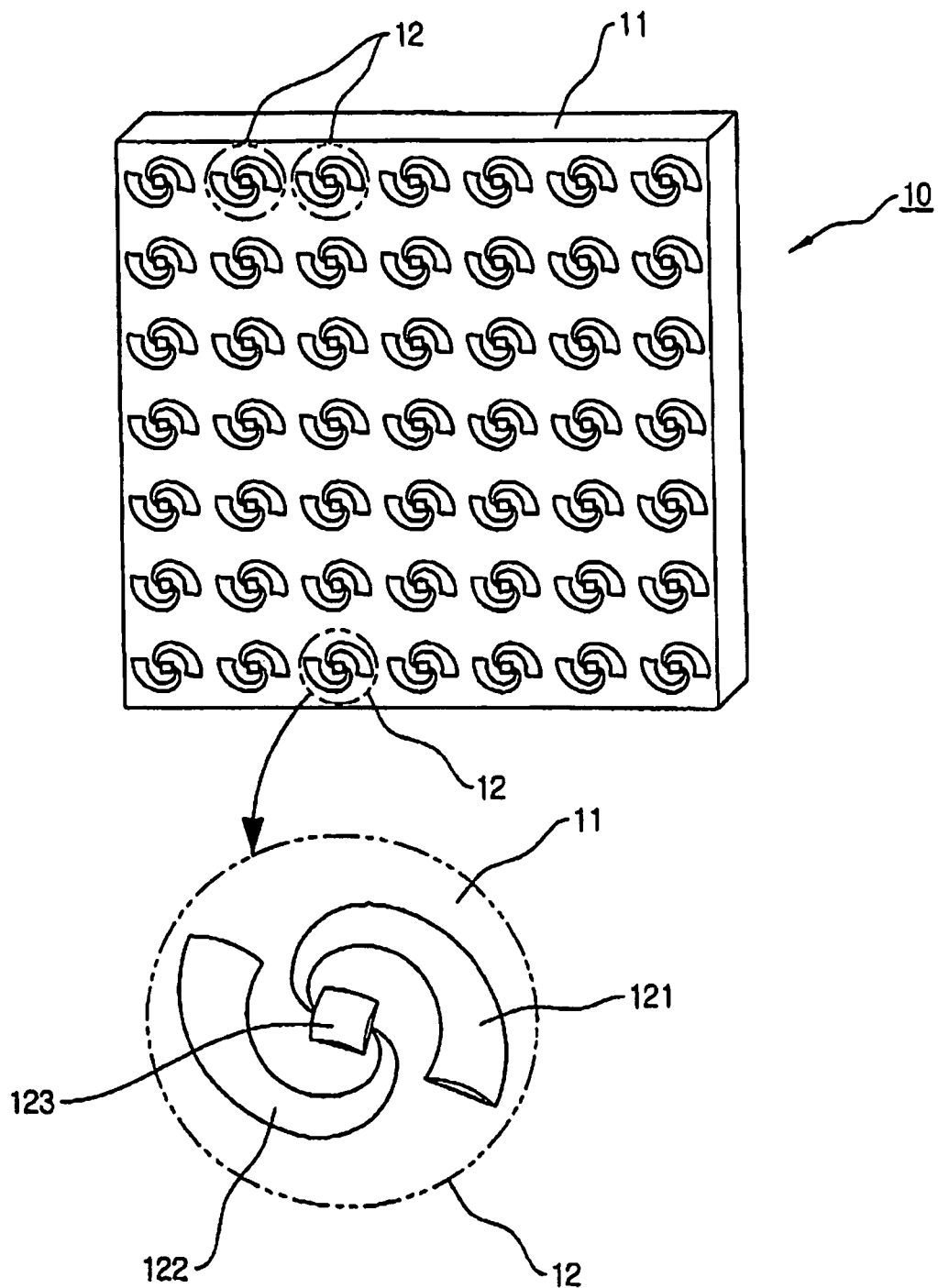

ELECTRONIC MIRROR AND METHOD FOR DISPLAYING IMAGE USING THE SAME

CROSS-REFERENCE TO RELATED APPLICATIONS

This application claims priority under 35 U.S.C. §119 to Korean Patent Application No. 10-2009-0006113, filed on Jan. 23, 2009, in the Korean Intellectual Property Office (KIPO), the entire contents of which are incorporated herein by reference.

BACKGROUND

1. Field

Exemplary embodiments relate to an electronic mirror and a method for displaying an image using the electronic mirror.

2. Description of the Related Art

A human body emits electromagnetic waves in various wavelength bands. Analysis of electromagnetic waves emitted from a human body may give information of the physical condition of each part of the human body. For example, an object having a temperature emits an infrared (IR) ray with a wavelength corresponding to the temperature. Thus, IR rays emitted from a human body may be used to recognize the change of body temperature or the change in temperature of local skin, which may be used to find a health condition and to check a degree of fatigue.

A terahertz wave may pass through various kinds of dielectric substances such as paper and plastic since it has a relatively longer wavelength than IR. Thus, terahertz waves emitted from a human body may be used to diagnose diseases not identified by the naked eyes, for example a progression of tooth decay, skin cancer and breast cancer. Also, the terahertz waves may be used to analyze, for example, a dielectric constant or refractive index of cells.

SUMMARY

Exemplary embodiments provide an electronic mirror capable of receiving a signal naturally emitted from a human body or object or a signal reflected from the human body or object to display the received signals as an image, and a method for displaying an image using the electronic mirror.

According to an exemplary embodiment, there is provided an electronic mirror. The electronic mirror may include a display unit which outputs an image; a detecting unit positioned in proximity to one side of the display unit and made of a transparent material, the detecting unit receiving a signal; and a control unit which controls the detecting unit and the display unit such that the signal received at the detecting unit is output as an image on the display unit.

According to another exemplary embodiment, the electronic mirror may further include a reflecting unit which is positioned in proximity to the other side of the display unit and reflects a light passing through the detecting unit and the display unit.

According to an exemplary embodiment, there is provided a method for displaying an image. The method for displaying an image may include receiving a signal at a detecting unit; displaying an image corresponding to the signal received at the detecting unit on a display unit; and outputting the image displayed on the display unit through the detecting unit.

According to another exemplary embodiment, the method for displaying an image may further include reflecting a light passing through the detecting unit and the display unit; and outputting the reflected light through the display unit and the detecting unit.

BRIEF DESCRIPTION OF THE DRAWINGS

The above and other features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 3 is a perspective view showing a detecting unit included in an electronic mirror according to example embodiments;

DETAILED DESCRIPTION

Figure 1:
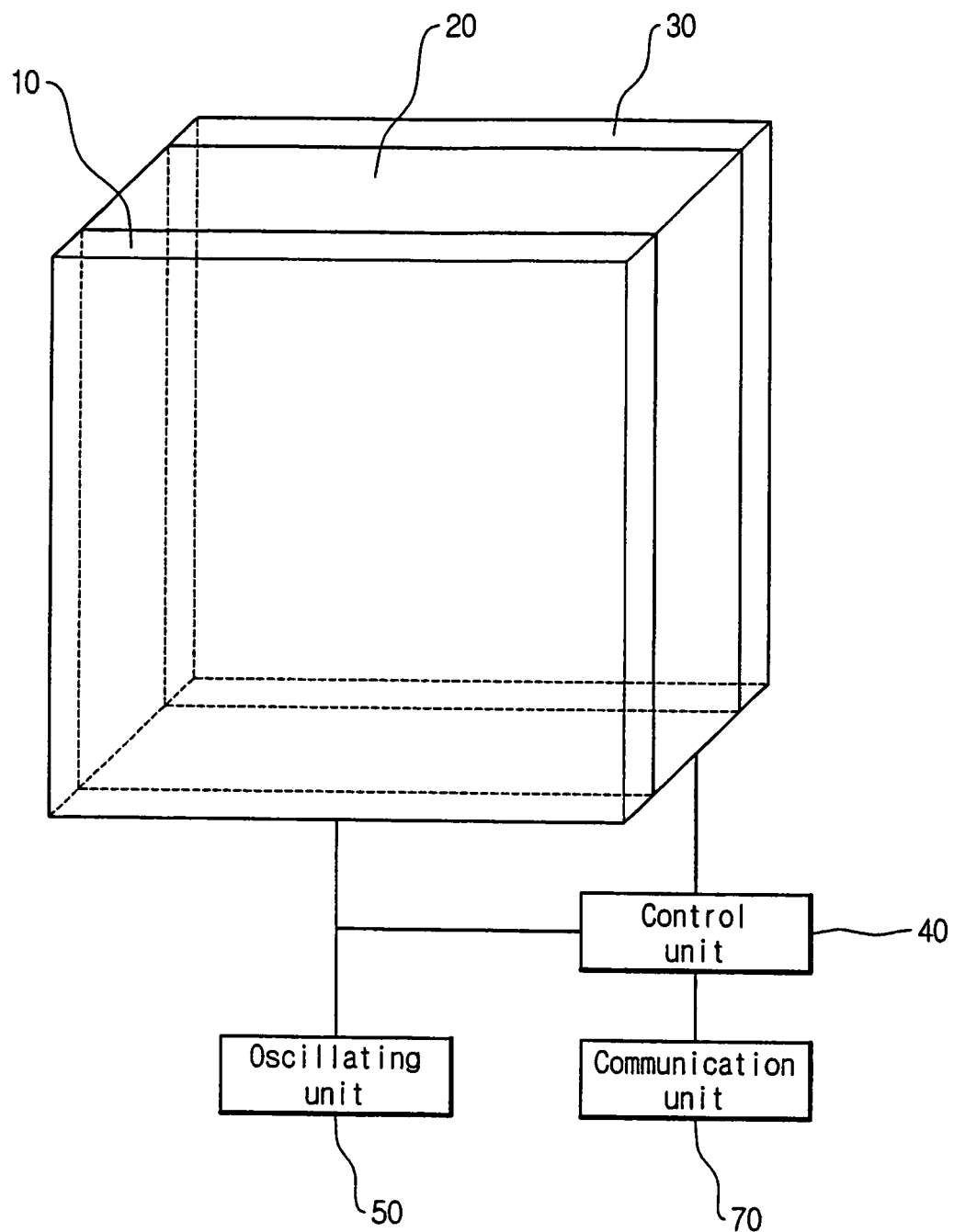
FIG. 1 is a schematic view showing an electronic mirror according to example embodiments.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 1 is a schematic view showing an electronic mirror according to example embodiments.

Referring to FIG. 1, the electronic mirror may include a detecting unit 10, a display unit 20 and a control unit 40. The detecting unit 10 may be a device for receiving signals emitted from an object or human body. The signal may be an electromagnetic wave in a predetermined wavelength band. For example, the detecting unit 10 may receive signals, in infrared (IR) or terahertz band, naturally emitted from an object or human body.

The electronic mirror may further include an oscillating unit 50 that generates an oscillation signal having a predetermined or reference wavelength. The detecting unit 10 may emit the oscillation signal generated by the oscillating unit 50 to the outside and receive the oscillation signal which is reflected by an outside object or human body and returned. Depending on wavelength bands, the signal naturally emitted from an object or human body may have a relatively weak intensity. Thus, an object or human body may be imaged by transmitting an oscillation signal to the outside using the oscillating unit 50 and receiving the reflected signal from the object or human body.

The signal received at the detecting unit 10 may be transmitted to the control unit 40. The control unit 40 may generate a control signal based on the received signal at the detecting unit 10 and operate the display unit 20 using the generated control signal. As a result, the signal received at the detecting unit 10 may be displayed on the display unit 20 as an image. For example, the signal received at the detecting unit may be displayed on the display unit 20 as an image pattern with different colors depending on wavelength, intensity or phase of the signal.

The display unit 20 may be a device for displaying an image. For example, the display unit 20 may include, for example, a cathode ray tube (CRT), a liquid crystal display (LCD), a plasma display panel (PDP), a reflective display panel, an electrochromic display, a nano dot display, a quantum dot display, an organic light emitting diode (OLED), or other suitable display devices. The control unit 40 may be configured as a circuit or computational device suitable for operating the display unit 20.

The detecting unit 10 may be positioned in proximity to one side of the display unit 20. The image displayed on the display unit 20 may be output from the electronic mirror through the detecting unit 10. For this purpose, the detecting unit 10 may be partially or entirely made of a transparent material.

The signal received at a specific region of the detecting unit 10 may be displayed on the display unit 20 at a corresponding region. Thus, if a human body or object is located in proximity to the detecting unit 10, an image may be displayed at a region of the display unit 20 corresponding to the location of the human body or object.

Through the aforesaid configuration, an image corresponding to a signal of an object or human body located in proximity to the electronic mirror may be displayed on the electronic mirror. For example, a signal in the IR or terahertz band emitted or reflected from a human body may be displayed as an image. A user may observe his/her image through the electronic mirror in real time based on the signal in the IR or terahertz band.

Meanwhile, the electronic mirror may include a communication unit 70 for transmitting the signal received at the detecting unit 10 to the outside. The communication unit 70 may be a device for wired or wireless communication. For example, the communication unit 70 may be a device for transmitting or receiving a signal using, for example, a local area network (LAN), radio frequency (RF), Bluetooth, Zigbee or wireless Internet (e.g., Wi-Fi). Signals in the IR or terahertz band emitted from a human body may be utilized as data for diagnosing health status. Thus, the signal received at the detecting unit 10 may be transmitted to, for example, a medical institution through the communication unit 70 for more precise analysis.

According to example embodiments, the electronic mirror may include a reflecting unit 30 positioned at a side opposite to the side where the detecting unit 10 is located with reference to the display unit 20. The reflecting unit 30 may be a device for reflecting an incident light. At this time, the display unit 20 may be switched between a first state of displaying an image and a second state of not displaying an image. For example, a user may switch the state of the display unit 20 by means of a specific mechanical or electrical input.

In case the display unit 20 is in the first state, the signal received at the detecting unit 10, or information corresponding to the received signal, may be displayed as an image on the display unit 20. Thus, an external light may not reach the reflecting unit 30. However, if the display unit 20 is in the second state, an image is not displayed on the display unit 20, so a light from an object or human body may reach the reflecting unit 30 through the detecting unit 10 and the display unit 20. The light reaching the reflecting unit 30 may be reflected thereon and output from the electronic mirror through the display unit 20 and the detecting unit 10 again. Thus, a user may observe a reflected figure of an object or human body using the electronic mirror.

Figure 2A:
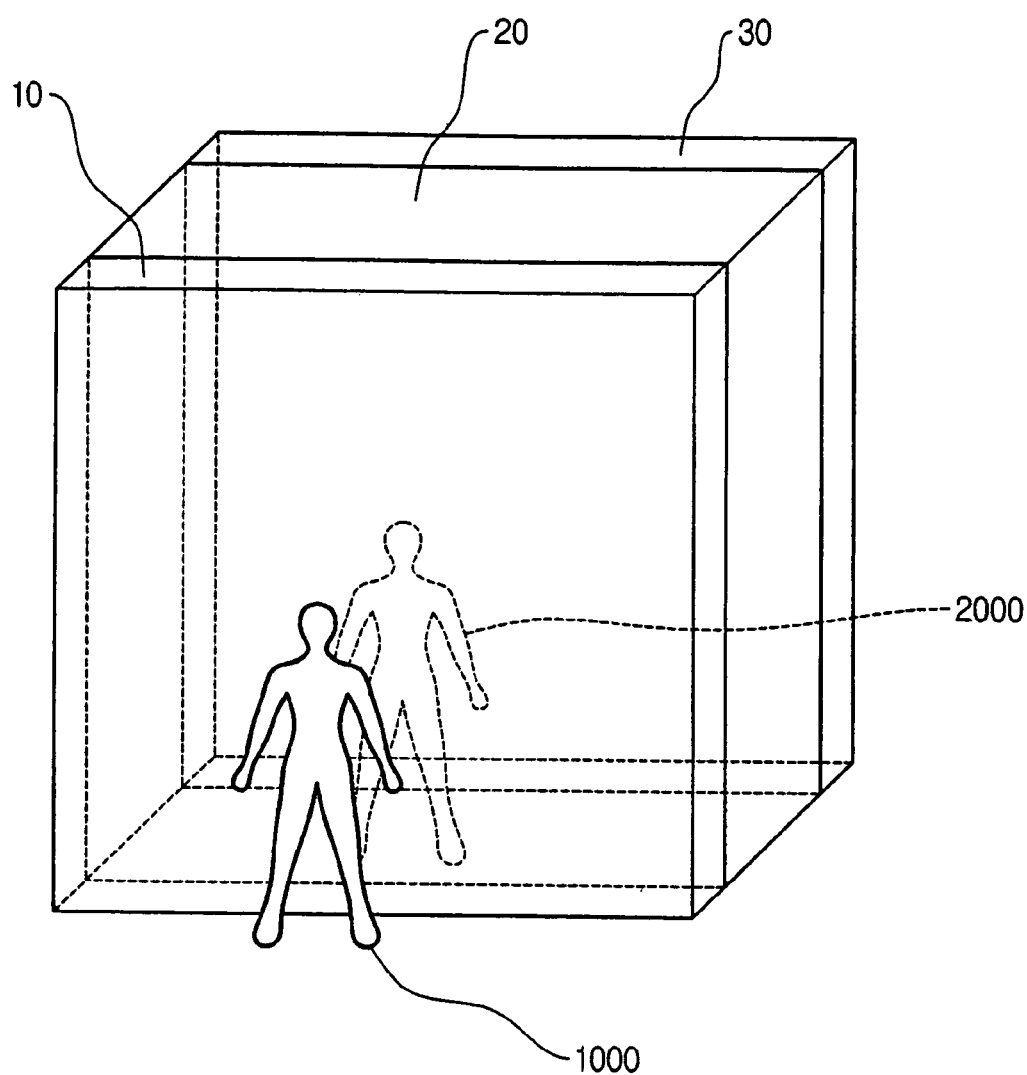
FIGS. 2A and 2B are schematic views showing a display unit included in an electronic mirror according to example embodiments.

FIG. 2A is a schematic view showing a state in which an image is displayed on the display unit of an electronic mirror according to example embodiments.

Referring to FIG. 2A, an object 1000 may be located in proximity to the electronic mirror. The object may be any object or, for example, a human body. If a signal naturally emitted from the object 1000 or reflected from the object 1000 is received at the detecting unit 10, the display unit 20 may output the received signal, or information corresponding to the received signal, as an image 2000. As mentioned above, the detecting unit 10 may be partially or entirely made of a transparent material such that the image 2000 output from the display unit 20 may pass through the detecting unit 10.

As a result, using the electronic mirror, a user may see an image corresponding to the signal emitted or reflected from an object. For example, if a user is located in front of the electronic mirror, the user may see images corresponding to signals in the IR or terahertz band emitted or reflected from his/her body as an image. The signals in IR or terahertz band emitted or reflected from a human body may be related to health status of each organ. Thus, the user may self-diagnose health status of his/her body using the electronic mirror.

Figure 2B:
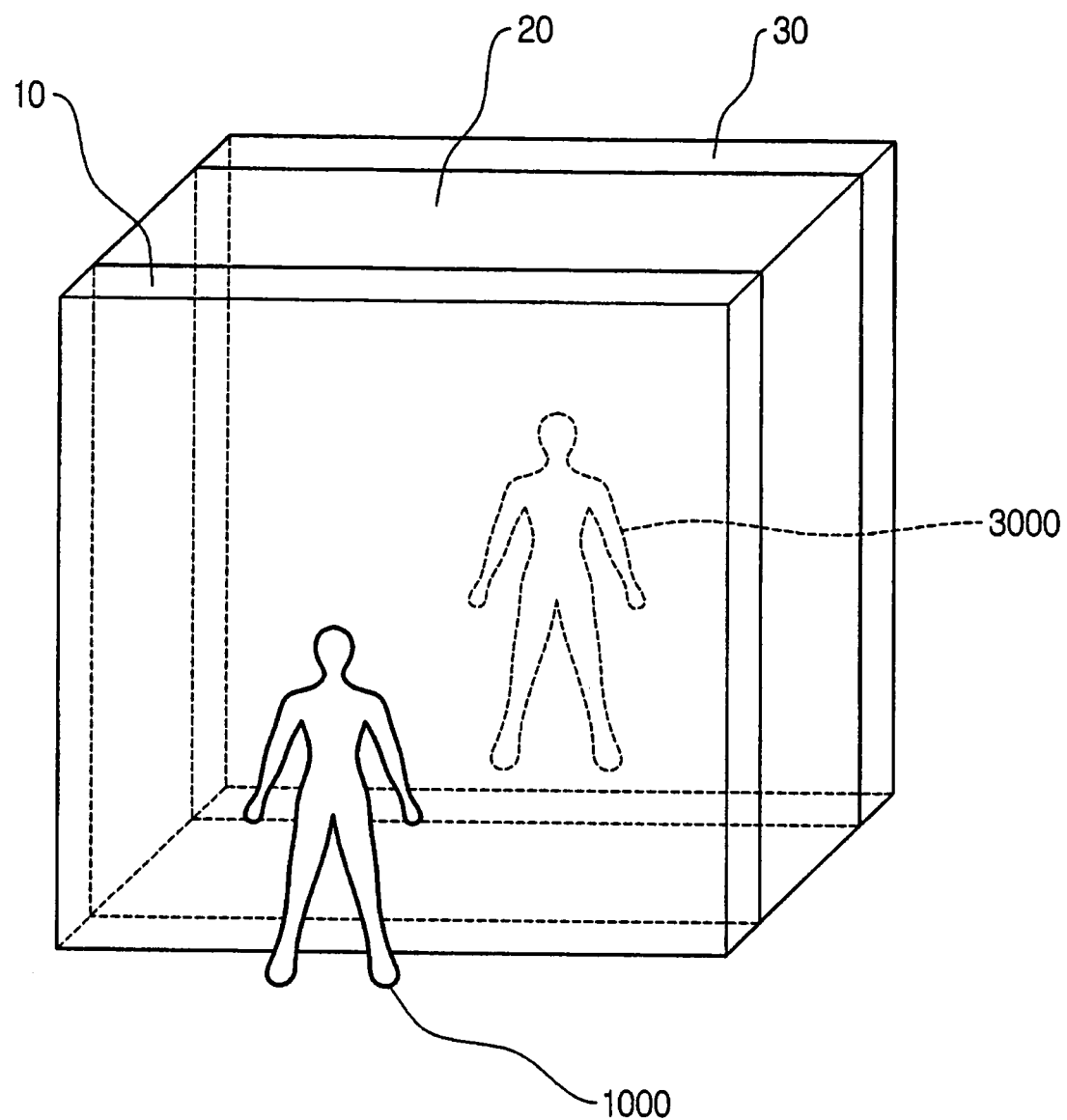

FIG. 2B is a schematic view showing a state in which an image is not displayed on the display unit of an electronic mirror according to example embodiments.

Referring to FIG. 2B, the display unit 20 may be partially or entirely made of a transparent material in a state where an image is not displayed. Thus, a light from the object 1000 may pass through the detecting unit 10 and the display unit 20. The light passing through the detecting unit 10 and the display unit 20 may be reflected on the reflecting unit 30 to form a mirror image 3000. Thus, the electronic mirror may be used similarly to a common mirror.

FIG. 3 is a perspective view showing an example configuration of the detecting unit included in an electronic mirror according to example embodiments.

Referring to FIG. 3, the detecting unit 10 may include a substrate 11, and at least one detector 12 on the substrate 11. The substrate 11 may be made of a transparent material such as glass. The detector 12 may be a device for receiving a signal in a desired wavelength band. The at least one detector 12 may be arranged in an array pattern. Since the detecting unit is configured with at least one detector 12 arranged in an array pattern, a specific location of the detecting unit 10 at which the signal is received may be specified.

The detector 12 may include a pair of antennas 121 and 122 electrically separated from each other. If an electromagnetic wave is propagated to the detector 12, an electric field may be formed between the antennas 121 and 122 due to the electromagnetic wave. Thus, an electric signal may be generated from the propagated electromagnetic wave. The control unit 40 (see FIG. 1) may be electrically connected between the antennas 121 and 122 to receive signals.

Antennas 121 and 122 may each be made of a conductive material. The material of antennas 121 and 122 may also be transparent. For example, each antenna 121 and 122 may be made of indium tin oxide (ITO), carbon nanotube (CNT), graphene, conductive polymer, nanofiber, nanocomposite, or other suitable materials.

In the example illustrated in FIG. 3, the detector 12 which includes spiral antennas 121 and 122. However, according to example embodiments the antennas 121 and 122 may be spiral antennas with a different shape from that shown FIG. 3 including, for example, log-periodic antennas, or other kinds of antennas with suitable shapes. Alternatively, according to example embodiments the detector 12 may include an IR camera or a terahertz camera.

Meanwhile, the detector 12 may further include a converter 123 electrically connected between the antennas 121 and 122. An electric signal received by each of the antennas 121 and 122 may be converted into a signal of other suitable form using the converter 123.

For example, the converter 123 may convert a signal received by each the antennas 121 and 122 into another signal corresponding to an intensity or phase of the received signal. Also, the converter 123 may include a PN junction. An electric signal received by the antennas 121 and 122 may be an AC signal. The AC signal may be converted into a DC signal using the converter 123 with a PN junction. Alternatively, the converter 123 may include an element for converting an electric signal into heat, such as a bolometer or a pyrometer.

Referring to the example is illustrated in FIG. 3, the converter 123 may be located on the substrate 11. Alternatively, according to example embodiments, the converter 123 may be provided out of the substrate 11 and connected to each of the antennas 121 and 122 through a waveguide. For example, the converter 123 may be provided at the control unit 40 illustrated in FIG. 1.

Meanwhile, the detector 12 may transmit an oscillation signal generated by the oscillating unit 50 illustrated in FIG. 1 to the outside. For example, if an oscillation signal is applied between the pair of antennas 121 and 122, an electromagnetic wave may be emitted from the surface of the antennas 121 and 122. In this case, the electromagnetic wave emitted from the antennas 121 and 122 may be reflected on an outside object or human body, and the antennas 121 and 122 may generate an electric signal using the reflected and returned electromagnetic wave.

Figure 4:
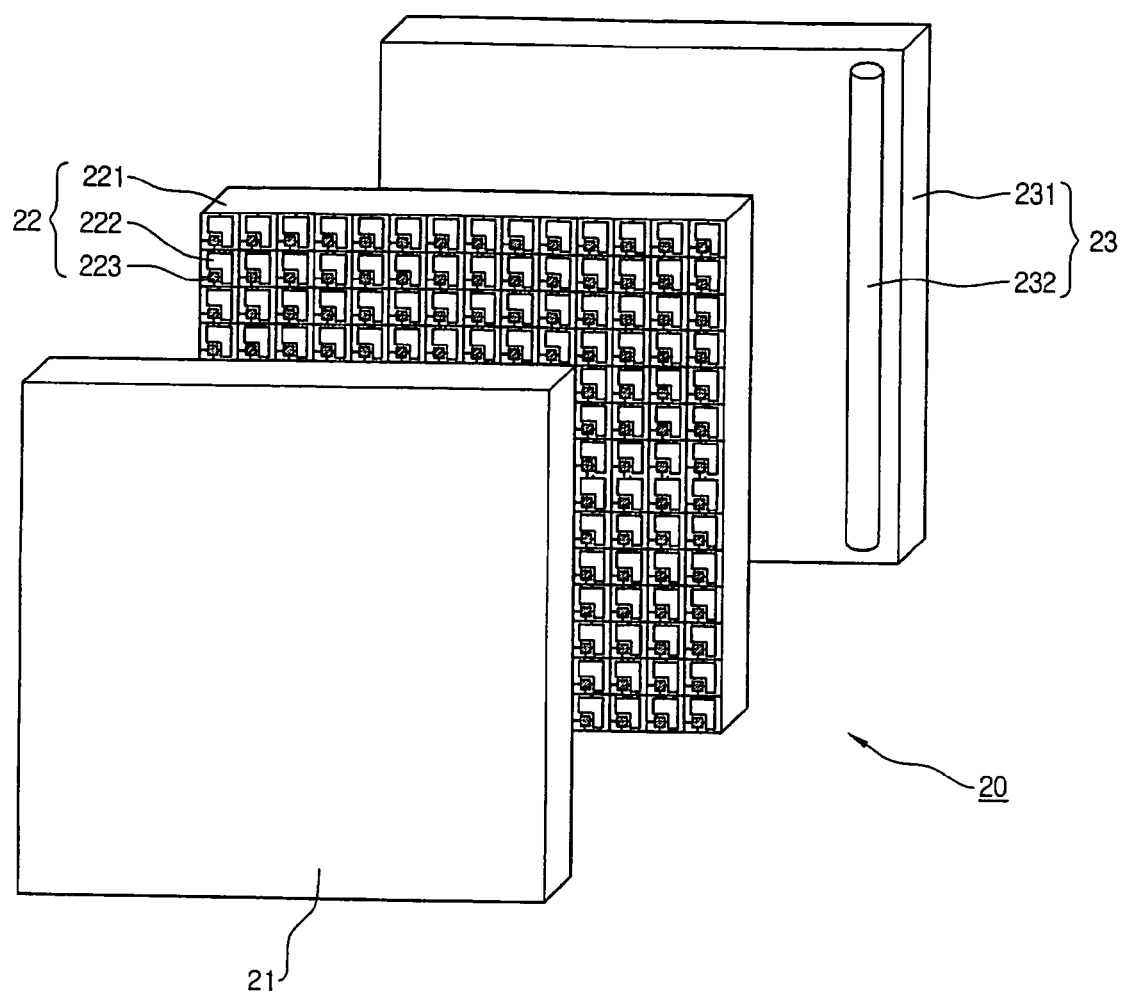
FIG. 4 is an exploded perspective view showing a display unit included in an electronic mirror according to example embodiments.

FIG. 4 is an exploded perspective view showing a detailed configuration of the display unit included in an electronic mirror according to example embodiments.

Referring to FIG. 4, the display unit 20 may include a color filter substrate 21, a thin film transistor (TFT) substrate 22, and a backlight unit 23.

The backlight unit 23 provides a light for displaying an image. The backlight unit 23 may include a reflective plate 231 and a lamp 232. The lamp 232 supplies light, and the light emitted from the lamp 232 may be reflected on the reflective plate 231 and then irradiated toward the TFT substrate 22. The backlight unit 23 may be configured with an edge lit structure in which the lamp 232 irradiates light at a side of the reflective plate 231. If the reflecting unit 30 illustrated in FIG. 1 is provided in the electronic mirror, the reflecting unit 30 may execute the same function as a general mirror. The reflecting unit 30 may function as a mirror using an external light reflected thereon.

In addition, if the reflecting unit 30 illustrated in FIG. 1 is provided at the electronic mirror, the reflecting unit 30 may execute the same function as the backlight unit 23. According to example embodiments, an image may be displayed using the light reflected on the reflecting unit 30, so an additional light source such as the lamp 232 may not be required. Thus, if the reflecting unit 30 is provided, the display unit 20 may not have the backlight unit 23.

The TFT substrate 22 may include a substrate 221, a pixel region 222 and a TFT 223. The substrate 221 may be made of a transparent material such as glass. The pixel region 222 may be arranged in an array pattern composed of at least one column and at least one row on the substrate 221. The TFT 223 may control operation of each pixel region 222. Also, the pixel region 222 and the TFT 223 may be electrically controlled by the control unit 40 illustrated in FIG. 1. The control unit 40 may control the pixel region 222 and the TFT 223 to display on the pixel region 222 an image corresponding to the signal received at the detecting unit 10 illustrated in see FIG. 1.

Referring to FIGS. 3 and 4, the detecting unit 10 may include a plurality of detectors 12. A signal received by each detector 12, or information corresponding to each of the received signals, may be displayed as an image at a pixel region located in proximity to each detector 12. Depending on the size of the pixel region 222, an image corresponding to a signal received by one detector 12 may be displayed at a plurality of pixel regions 222. Alternatively, an image corresponding to a signal received by a plurality of detectors 12 may be displayed at one pixel region 222.

The color filter substrate 21 may be positioned to cover the TFT substrate 22. In order to express a color of an image, the color filter substrate 21 may have color filters corresponding to each pixel region 222. In addition, an electrochromic material may be applied to the color filter substrate 21 such that the color filter substrate 21 exhibits a color only when an electric field is applied thereto and the color filter substrate 21 is colorless when there is no electric field, such that the reflective plate 231 or the reflecting unit 30 illustrated in FIG. 1 may operate as a mirror.

Referring to the example explained above with reference to FIG. 4, the electronic mirror may have an LCD-type display. Alternatively, according to example embodiments, the display unit may be, for example, a reflective display panel, an electrochromic display, a CRT, a PDP, a nano dot display, a quantum dot display, an OLED, or other suitable display devices.

Figure 5:
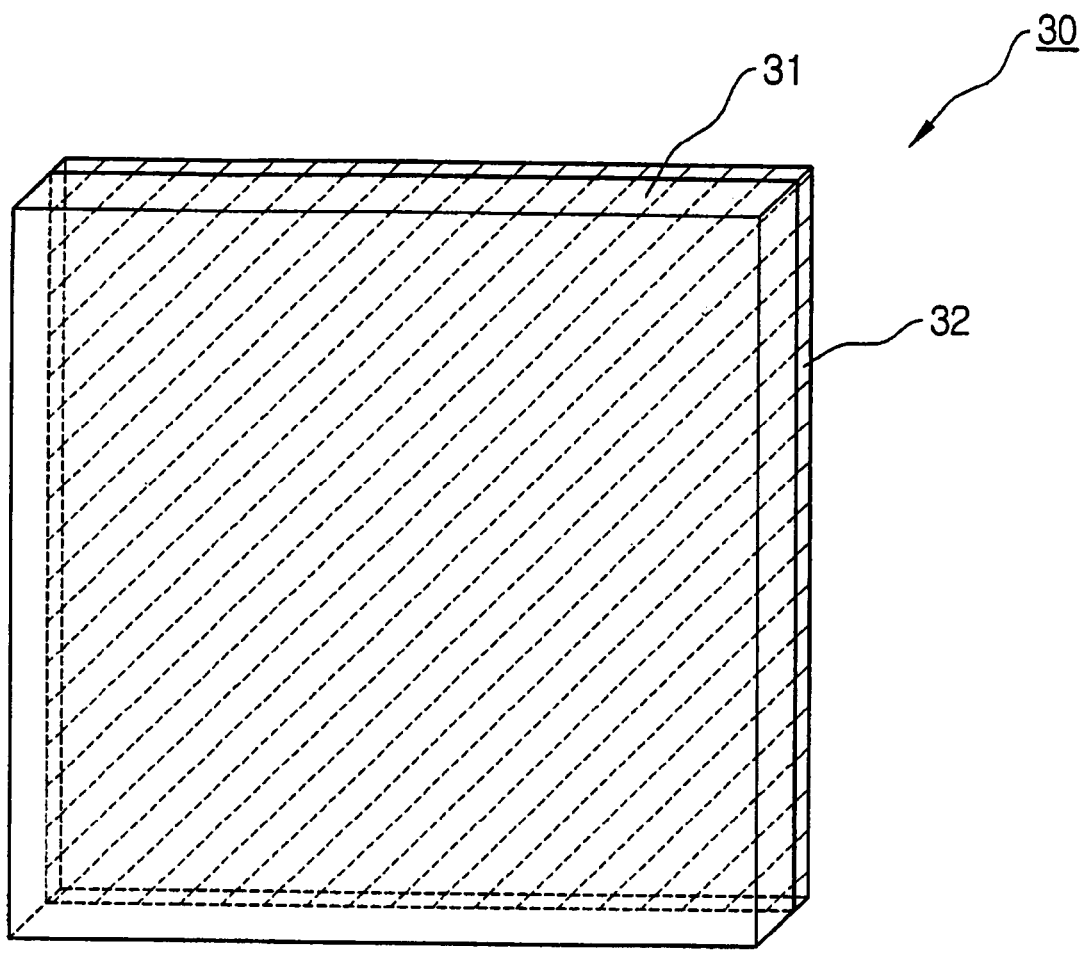
FIG. 5 is a perspective view showing a reflecting unit included in an electronic mirror according to example embodiments.

FIG. 5 is a perspective view showing a detailed configuration of the reflecting unit included in an example embodiment of an electronic mirror.

Referring to FIG. 5, the reflecting unit 30 may include a substrate 31 and a reflective material 32. The substrate 31 may be made of a transparent material such as glass. The reflective material 32 may be formed on one side of the substrate 31. For example, the reflective material 32 may be made of silver (Ag). If an image is not displayed on the display unit 20 illustrated in see FIG. 1, a visible light from an object or human body may pass through the substrate 31. The light passing through the substrate 31 may be reflected on the reflective material 32 and output from the electronic mirror.

While the example embodiments have been shown and described, it will be understood by those skilled in the art that various changes in form and details may be made thereto without departing from the spirit and scope of this disclosure as defined by the appended claims.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. An electronic mirror, comprising:
   a display unit;
   a detecting unit positioned in proximity to a first side of the display unit, the detecting unit including a transparent material, the detecting unit being configured to receive a signal unit including a light generating unit configured to generate light, and an array of light control elements configured to display an image by controlling an amount of light that passes from the light generating unit through the array of light control elements;
   a control unit configured to control the display unit to output an image, the image being based on the signal received at the detecting unit, the detecting unit being configured such that light that is output by the display unit and corresponds to the output image is incident on, and visible through, the transparent material of the detecting unit; and
   a reflecting unit which is positioned in proximity to a second side of the display unit, the electronic mirror being configured such that the reflecting unit reflects a light passing through the detecting unit and the display unit,
   wherein the display unit is configured to operate while switching between a first state and a second state, wherein the image based on the signal received at the detecting unit it outputted on the display unit in the first state, and wherein the image is not outputted on the display unit in the second state, such that the light reflected by the reflecting unit is viewable through the display unit.

2. The electronic mirror according to claim 1, wherein the display unit is positioned in between the reflecting unit and the detecting unit.

3. The electronic mirror according to claim 2, wherein the display unit is made of a transparent material.

4. The electronic mirror according to claim 1, wherein the detecting unit includes a substrate made of a transparent material and a plurality of detectors arranged on the substrate in an array pattern.

5. The electronic mirror according to claim 4, wherein each of the plurality of the detectors includes an antenna.

6. The electronic mirror according to claim 5, wherein the antenna is a spiral antenna or a log-periodic antenna.

7. The electronic mirror according to claim 4, wherein each of the plurality of detectors is made of a transparent conductive material.

8. The electronic mirror according to claim 7, wherein each of the plurality of detectors is made of at least one selected from a group including indium tin oxide, carbon nanotube, graphene, conductive polymer, nanofiber, nanocomposite, and any mixtures thereof.

9. The electronic mirror according to claim 1, wherein the detecting unit includes an infrared (IR) camera or a terahertz camera.

10. The electronic mirror according to claim 1, further comprising an oscillating unit configured to generate an oscillation signal,
    wherein the detecting unit is configured to transmit the oscillation signal generated by the oscillating unit to the outside, and receive the oscillation signal which is reflected from an outside object.

11. The electronic mirror according to claim 1, further comprising a communication unit configured to transmit the signal received at the detecting unit.

12. The electronic mirror according to claim 1, wherein the display unit includes at least one selected from a group including a cathode ray tube, a liquid crystal display, a plasma display panel, a reflective display panel, an electrochromic display, a nano dot display, a quantum dot display or an organic light emitting diode and any combinations thereof.

13. The electronic mirror according to claim 1, wherein the signal includes a signal in an IR or terahertz band.

14. The electronic mirror according to claim 1, wherein the display unit is configured to operate while switching between a first state and a second state, wherein the image based on the signal received at the detecting unit it outputted on the display unit in the first state, and wherein the image is not outputted on the display unit in the second state such that the light reflected by the reflecting unit is viewable through the display unit.

15. A method for displaying an image, comprising:
    receiving a signal at a detecting unit including a transparent material;
    displaying an image corresponding to the signal received at the detecting unit on a display unit such that light that is output by the display unit and corresponds to the displayed image is incident on, and visible through, the transparent material of the detecting unit, the display unit including a light generating unit configured to generate light, and an array of light control elements configured to display an image by controlling an amount of light that passes from the light generating unit through the array of light control elements;
    outputting the image displayed on the display unit through the detecting unit;
    reflecting, with a reflecting unit, a light passing through the detecting unit and the display unit; and outputting the reflected light through the display unit and the detecting unit,
wherein the displaying an image includes operating the display unit while switching between a first state and a second state, wherein the image corresponding to the received signal is outputted on the image displaying unit in the first state, and wherein the image is not outputted on the display unit in the second state, such that the light reflected by the reflecting unit is viewable through the image displaying unit.

16. The method for displaying an image according to claim 15, wherein the display unit is positioned in between the detecting unit and the reflecting unit reflecting the light passing through the detecting unit and the display unit.

17. The method for displaying an image according to claim 15, further comprising:
transmitting an oscillation signal to the outside before receiving the signal received at the detecting unit,
wherein the signal received at the detecting unit is the oscillation signal which is reflected from an outside object.

18. The method for displaying an image according to claim 15, wherein receiving the signal at the detecting unit includes converting an electromagnetic wave from the outside into an electric signal.

19. The method for displaying an image according to claim 15, further comprising:
transmitting the signal received at the detecting unit.

20. The method for displaying an image according to claim 15, wherein the signal includes a signal in an IR or terahertz band.

21. A display device comprising:
a signal receiving unit including a transparent material and configured to receive a signal from an object in front of the signal receiving unit; and
an image displaying unit on one side of the signal receiving unit, the image displaying unit including a light generating unit configured to generate light, and an array of light control elements configured to display an image by controlling an amount of light that passes from the light generating unit through the array of light control elements, the image displaying unit being configured to display an image viewable through the signal receiving unit such that light that is output by the display unit and corresponds to the displayed image travels towards the object via the transparent material of the signal receiving unit, the displayed image being based on the received signal; and
a reflecting unit on one side of the image displaying unit, the display device being configured such that the reflecting unit reflects a light passing through the signal receiving unit and the image displaying unit,
wherein the image displaying unit is further configured to operate while switching between a first state and a second state, wherein the image based on the received signal is outputted on the image displaying unit in the first state, and wherein the image is not outputted on the image displaying unit in the second state, such that the light reflected by the reflecting unit is viewable through the image displaying unit.

22. The display device according to claim 21, wherein the signal receiving unit is made of a transparent material.

23. The display device according to claim 22, wherein the signal receiving unit includes a substrate made of a transparent material and a plurality of transparent detectors arranged on the substrate, the received signal being received by the transparent detectors.

24. The display device according to claim 21, wherein the display unit is positioned in between the signal receiving unit and the image displaying unit.

25. The display device according to claim 21, further comprising an oscillating unit which generates an oscillation signal, wherein the signal receiving unit is configured to transmit the oscillation signal generated by the oscillating unit toward the front of the signal receiving unit, and receive the oscillation signal which is reflected from an object in front of the signal receiving unit.

26. The display device according to claim 21, wherein the image displaying unit is further configured to operate while switching between a first state and a second state, wherein the image based on the received signal is outputted on the image displaying unit in the first state, and wherein the image is not outputted on the image displaying unit in the second state such that the light reflected by the reflecting unit is viewable through the image displaying unit.

* * * * *